United States Patent
Rudzevich et al.

(10) Patent No.: US 10,352,898 B2
(45) Date of Patent: Jul. 16, 2019

(54) CAPILLARY IONIC TRANSISTOR

(71) Applicant: UNIVERSITY OF CENTRAL FLORIDA RESEARCH FOUNDATION, INC., Orlando, FL (US)

(72) Inventors: Yauheni Rudzevich, Oviedo, FL (US); Yuqing Lin, Orlando, FL (US); Lee Chow, Orlando, FL (US)

(73) Assignee: UNIVERSITY OF CENTRAL FLORIDA RESEARCH FOUNDAING, INC., Orlando, FL (US)

( * ) Notice: Subject to any disclaimer, the term of this patent is extended or adjusted under 35 U.S.C. 154(b) by 14 days.

(21) Appl. No.: 15/121,440

(22) PCT Filed: Feb. 26, 2015

(86) PCT No.: PCT/US2015/017637
§ 371 (c)(1),
(2) Date: Aug. 25, 2016

(87) PCT Pub. No.: WO2015/130874
PCT Pub. Date: Sep. 3, 2015

(65) Prior Publication Data
US 2016/0363559 A1    Dec. 15, 2016

Related U.S. Application Data

(60) Provisional application No. 61/944,753, filed on Feb. 26, 2014.

(51) Int. Cl.
*G01N 27/447* (2006.01)
*B01L 3/00* (2006.01)
*G01N 27/414* (2006.01)
*B01L 3/02* (2006.01)

(52) U.S. Cl.
CPC ........ *G01N 27/44752* (2013.01); *B01L 3/021* (2013.01); *B01L 3/50273* (2013.01);
(Continued)

(58) Field of Classification Search
CPC ..... G01N 27/447–27/44795; B01D 57/00–02; C02F 1/4696; B81B 1/00–008
(Continued)

(56) References Cited

U.S. PATENT DOCUMENTS 5,092,972 A * 3/1992 Ghowsi ............ G01N 27/44752
204/454
6,331,235 B1 * 12/2001 Dolphin ........... G01N 27/44747
204/451

(Continued)

FOREIGN PATENT DOCUMENTS

WO    2008039579    4/2008
WO    2012122029    9/2012

OTHER PUBLICATIONS

Abgrall, Patrick et al., Nanofluidic Devices and Their Potential Applications, Microfluidic Devices in Nanotechnology: Fundemental Concepts, Jul. 15, 2010, pp. 155-214.

(Continued)

*Primary Examiner* — Bach T Dinh
(74) *Attorney, Agent, or Firm* — Bond, Schoeneck & King PLLC; Erin Phillips; William Greener (57) ABSTRACT

A capillary ionic transistor and method of using is disclosed. The method including providing a capillary pipette (100) having an inner surface defining a channel, and a conductive layer disposed (102) about electrode the channel; filling at least a portion of the channel with an ionic solution (110) such that an electrical double layer forms on the inner surface of the pipette; inducing an electric potential within the ionic solution sufficient to generate a longitudinal flow of (Continued)

ions within the channel; and inducing an electric potential in the conductive layer sufficient to alter the zeta potential of the electrical double layer and adjust the flow of ions within the ionic solution.

18 Claims, 5 Drawing Sheets

(52) U.S. Cl.
CPC ... *G01N 27/4146* (2013.01); *G01N 27/44791* (2013.01); *B01L 3/02* (2013.01); *B01L 2300/0838* (2013.01); *B01L 2300/0887* (2013.01); *B01L 2300/0896* (2013.01); *B01L 2300/16* (2013.01); *B01L 2400/0415* (2013.01)

(58) Field of Classification Search
USPC ............... 204/450–470, 546–550, 600–621, 204/643–645
See application file for complete search history.

(56) References Cited

U.S. PATENT DOCUMENTS

| | | | |
|---|---|---|---|
| 8,105,471 B1* | 1/2012 | Han | G01N 27/44752 204/451 |
| 2004/0058423 A1* | 3/2004 | Albritton | G01N 27/44743 435/173.7 |
| 2006/0104311 A1 | 5/2006 | Soga et al. | |
| 2014/0031995 A1* | 1/2014 | Kawai | G01N 27/447 700/282 |

OTHER PUBLICATIONS

International Search Report and Written Opinion Form PCT/ISA/220, International Application No. PCT/US2015/017637, pp. 1-14, International Filing Date Feb. 26, 2015.

* cited by examiner

CAPILLARY IONIC TRANSISTOR

REFERENCE APPLICATION DATA

The present application claims the benefit of U.S. provisional patent application No. 61/944,753, filed Feb. 26, 2014, which is hereby incorporated by reference in its entirety.

GOVERNMENT FUNDING

Funding for the invention was provided by the National Science Foundation under award NSF 0901361. The government has certain rights in the invention.

FIELD OF THE DISCLOSURE

The present disclosure relates generally to ionic transistors, and in more particular aspects, to ionic transistors employing a capillary pipette.

BACKGROUND

The ability to control ionic and molecular transport in nanochannels is of particular interest in the fields of physics and chemistry. To this end, nanofluidic devices such as ionic diodes and ionic transistors form important elements in applications such as ionic transport regulating systems. These devices are also important in biotechnological applications such as separation sensing and drug delivery, for example, intracellular implantation.

An ionic transistor is a device that enables control of ionic current through a nanochannel in both directions by a small change in gate voltage. Current ionic transistors have been fabricated using techniques such as FIB drilling, etching, lithography and nanowire growing. However, these techniques are expensive and complex. Accordingly, there is a need in the art for an ionic transistor that is less costly and relatively simpler to fabricate.

SUMMARY

The present disclosure is directed to an inexpensive and simply fabricated ionic transistor. Accordingly, the embodiments herein are directed an ionic transistor cheaply and easily formed from a capillary pipette. In one aspect, a method for controlling the transport of ions through a channel, comprises the steps of: providing a capillary pipette having an inner surface defining a channel, and a conductive layer disposed about the channel; filling at least a portion of the channel with an ionic solution such that an electrical double layer forms on the inner surface of the pipette; inducing an electric potential within the ionic solution sufficient to generate a longitudinal flow of ions within the channel; inducing an electric potential in the conductive layer sufficient to alter the electrical double layer and adjust the flow of ions within the ionic solution.

According to an embodiment, the capillary pipette is dimensioned such that the electric double layer overlaps at at least one point.

According to an embodiment, the capillary pipette is dimensioned such that the electric double layer will overlap at least one point upon the application of a predetermined potential to the conductive layer.

According to an embodiment, the pipette is dimensioned to narrow at at least one point.

According to an embodiment, the narrow point of the pipette is minimally 10 nm in diameter and maximally 100 nm in diameter.

According to an embodiment, the narrow point is at a tip of the pipette 100.

According to an embodiment, the potential applied to the conductive layer causes the electrical double layer to widen, reducing the flow of ions within the channel.

According to an embodiment, the potential applied to the conductive layer causes the electrical double layer to narrow, enhancing the flow of current within the channel.

According to an embodiment, the conductive layer is comprised of one of chromium, aluminum, copper, or any other material capable of retaining a charge.

According to another aspect, a device for controlling the transport of ions through a channel, comprises: a capillary pipette having an inner surface defining a channel, wherein the pipette is adapted to form an electric double layer on the inner surface when filled with an ionic solution; a conductive layer positioned to exhibit an electric field within the channel when subjected to an electric charge, such that any electric double layer on the inner surface will be altered by the electric field.

According to an embodiment, the device further comprises a voltage source positioned to induce a longitudinal flow of ions in any ionic fluid at least partially filling the channel.

According to an embodiment, the device comprises a voltage source connected to apply a charge to the conductive layer.

According to an embodiment, the capillary pipette is dimensioned to cause the electric double layer to overlap when the channel is filled with an ionic solution.

According to an embodiment, the capillary pipette is dimensioned to cause the electric double layer to overlap when the channel is filled with an ionic solution and a predetermined charge is applied to the conductive layer.

According to an embodiment, the capillary pipette is dimensioned to narrow at at least one point.

According to an embodiment, the narrow point is at the tip of the pipette 100.

According to an embodiment, the capillary pipette is minimally 10 nm in diameter and maximally 100 nm in diameter.

According to an embodiment, the conductive layer is comprised of one of chromium, aluminum, copper, or any other material capable of retaining a charge.

BRIEF DESCRIPTION OF THE DRAWINGS

The present invention will be more fully understood and appreciated by reading the following Detailed Description in conjunction with the accompanying drawings, in which.

DETAILED DESCRIPTION

Figure 1:
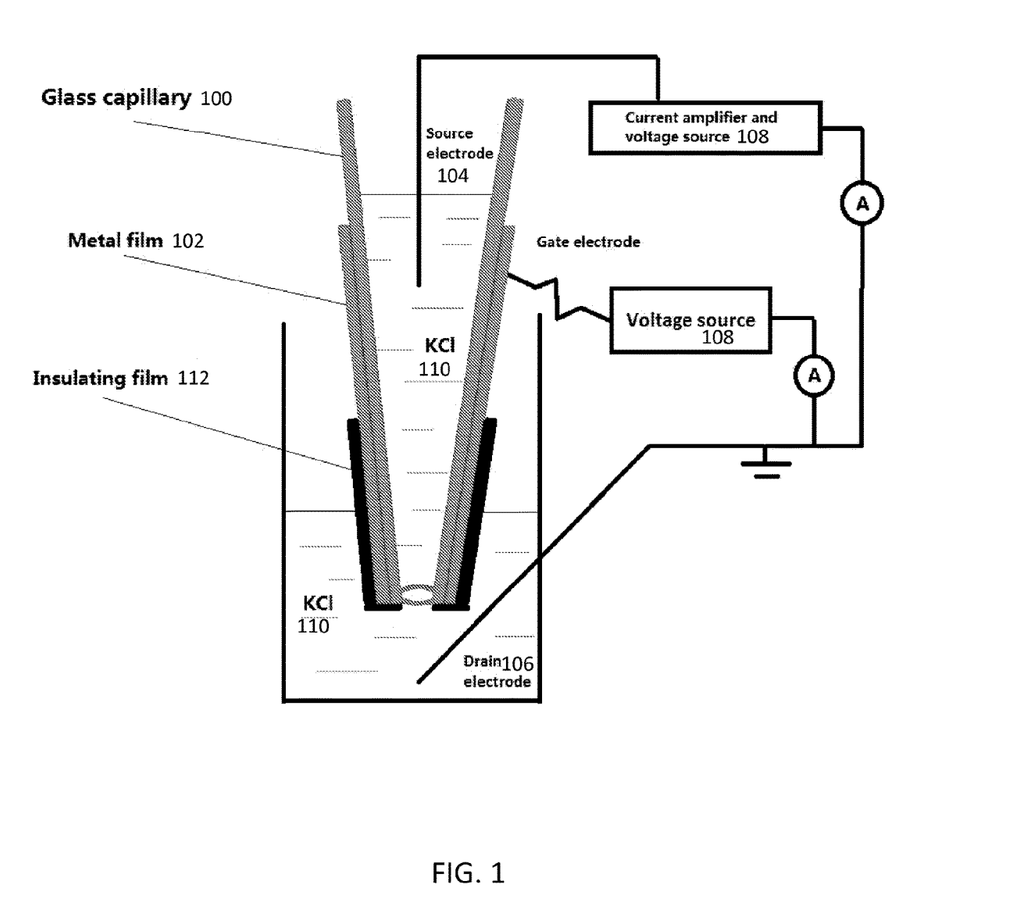
FIG. 1 shows a diagram of a capillary ionic transistor according to an embodiment of the present invention.

Referring now to the drawings, wherein like reference numerals refer to like parts throughout, there is seen in FIG. 1 a diagram of a system for controlling ionic current through a channel, according to an embodiment of the present invention. FIG. 1 shows an ionic transistor, comprising a capillary pipette 100, a gate 102, a source 104, a drain 106, and a voltage source 108 connected to gate 102. According to an embodiment, capillary pipette 100 defines an inner channel, with a diameter that can range from a minimum of 10 nm to a maximum of 100 nm value. In an exemplary embodiment, the inner channel is narrower at at least one point, such as the tip of the pipette 100. In use, capillary pipette 100 may be filled with, or otherwise placed in a bath of, an ionic solution 110.

Generally speaking, in operation, source 104 and drain 106 applies an electric potential difference within ionic solution 110. The electric potential, in turn, creates a current in the form of a flow of ions from one end of the channel to the other. Separately, ionic solution 110 naturally forms an electric double layer on the inner surface of the capillary 100. A potential applied to gate 102 generates an electric field within capillary pipette 100, changing the zeta potential of the electric double layer. As the zeta potential of electric double layer changes, the width of the electric double layer changes, limiting or, alternately, enhancing the flow of ions between the source and the drain 106.

Whether the current is limited or enhanced is dependent upon the polarity of the potential applied to the gate 102. If the gate 102 voltage is positive, the positive ions accumulated on the inner surface will repel from the surface, effectively shrinking the electric double layer and creating an open channel for the current to flow. By contrast, if the gate 102 voltage is negative, the width of the electric double layer will increase as a greater number of positive ions are attracted to the surface. The wider electric double layer will effectively create a barrier which limits the flow of current. In an exemplary embodiment, the pipette 100 is dimensioned such that, without a charge applied to the gate 102, the electric double layer will overlap at least one point, stopping or severely curtailing the flow of current through the channel. Accordingly, the flow of current will cease until a positive charge is applied to the gate 102 and the double layer recedes. In alternate embodiment, the pipette 100 is dimensioned such that the electric double layer will overlap upon the application of a negative charge to gate 102. One of ordinary skill will recognize that other factors, such as the composition of the pipette 100, the dimensions of gate 102, the conductivity of gate 102, the strength the potential applied to gate 102, and the concentration of ions in ionic solution 110 may all effect the width of the electric double layer and each may be tailored to achieve the desired current in the channel.

The capillary pipette 100 is fashioned, in the embodiment, from borosilicate glass; however, pipette 100 may be made from quartz or from any other material suitable for fabricating a pulled capillary micropipette 100. As mentioned above, one of ordinary skill will recognize that the composition of the pipette 100 will affect the naturally forming electric double layer. Accordingly, different materials may be selected to tailor the naturally formed electric double layer for the desired configuration of the ionic transistor.

Figure 3A:
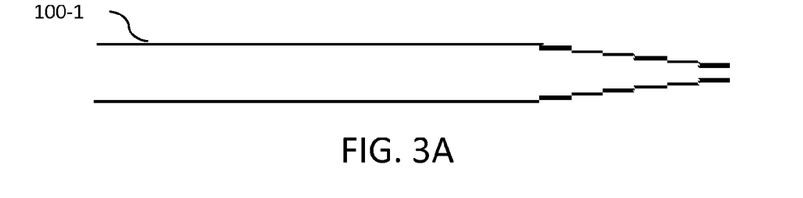
FIGS. 3A, 3B, and 3C show a diagram of a device according to separate embodiments of the present invention.
Figure 3B:
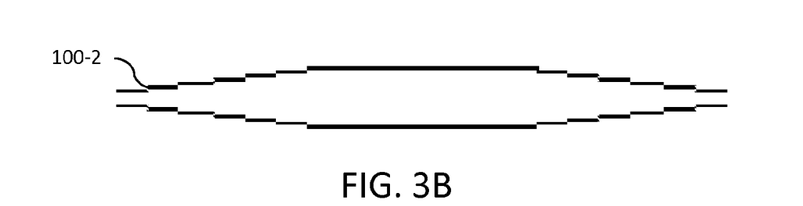
Figure 3C:
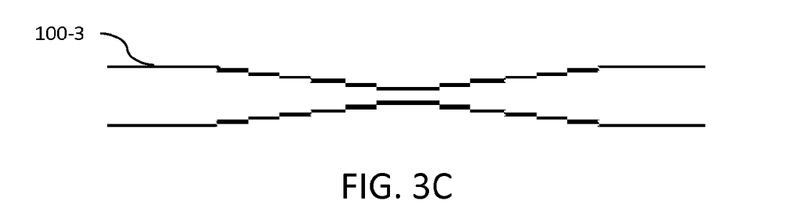

FIG. 3 shows several embodiments of capillary pipette 100. FIG. 3A shows capillary pipette 100-1 narrowing at one tip, according to one embodiment. FIG. 3B, according to another embodiment, shows a capillary pipette 100-2 narrowing at both tips. FIG. 3C shows a capillary pipette 100-3 with a narrow channel in the middle. Each embodiment may be best suited for different applications. Current flow through the pipette 100 pore has a preferable direction from small opening to wide, while current in reverse direction is suppressed. Thus, pipette 100-1 may be best suited in applications where current in one direction needs to be suppressed. By contrast, 100-2, having two tips, and 100-3 having the same tapering in both directions, may be best suited for applications where current should be suppressed in both directions. However a person of ordinary skill would recognize that these shapes are not exclusive, nor are the applications of the shapes limited to those suggested—the pipette 100 may be any combination of the shapes suggested as long as at least one point of capillary pipette 100 is narrow enough to cause the electric double layer to overlap when the pipette 100 is in use, and a voltage is applied to the gate 102. In an exemplary embodiment, the diameter of at least one point in the pipette 100 is comparable to the Debye length, or having a maximum of 100 nm.

In an exemplary embodiment, the gate 102 covers the entire outer surface of the capillary pipette 100. In an alternative embodiment, the gate 102 may only cover a portion, such as the tip or the center of the pipette 100. In the embodiment, the gate 102 may be implemented as a film or coating over capillary pipette 100. It will be obvious to a person of ordinary skill in the art that the thickness of the gate 102 can vary while maintaining its function of retaining a charge. In another embodiment, the gate 102 may consist of one or more wires, or a conductive surface housed in a sleeve and placed over capillary pipette 100. In an exemplary embodiment, the gate 102 may be placed over the narrowest point of the pipette 100. A person of ordinary skill in the art will recognize that the gate 102 may be placed in any fashion that would exhibit an electric field on the interior of the capillary pipette 100, to strengthen, or alternately weaken, the electric double layer.

Figure 2A:
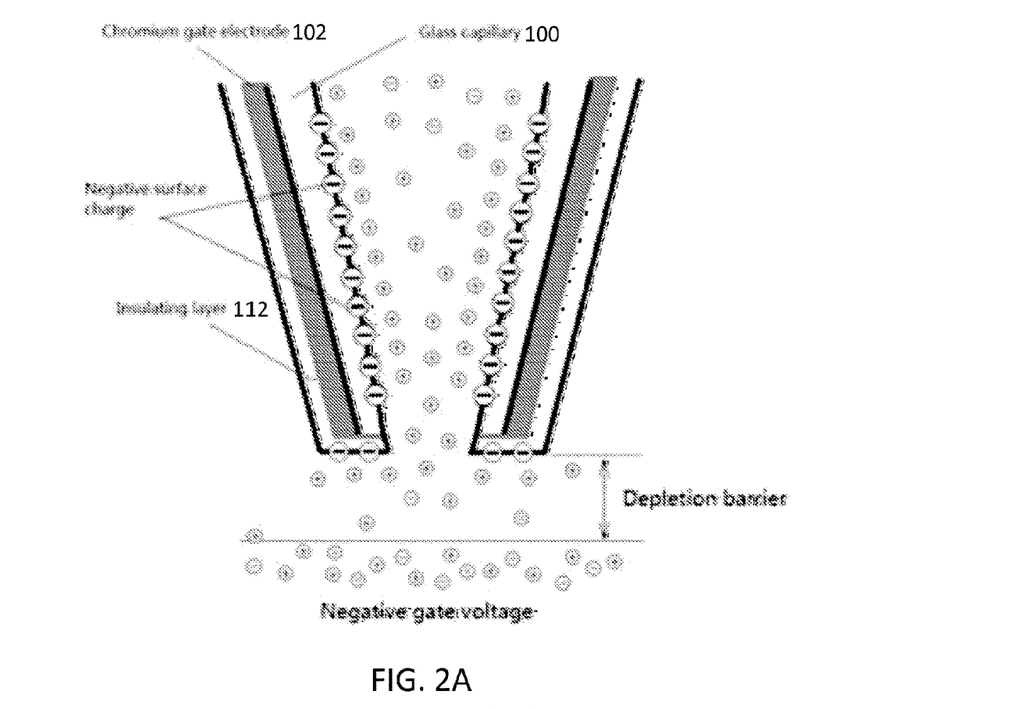
FIGS. 2A and 2B show a diagram of a system according to an embodiment of the present invention.
Figure 2B:
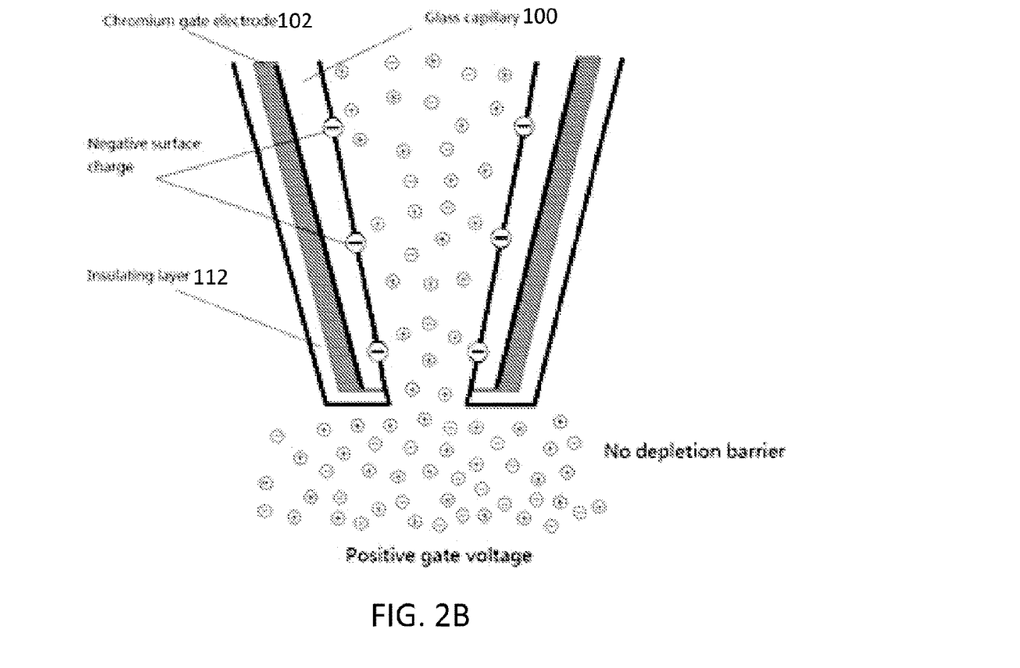

If the gate 102 is located near the end of the pipette 100, additional current suppressing behavior may arise due to a depletion barrier forming at the tip of the pipette 100. FIG. 2 demonstrates this behavior. Applying a negative potential to gate 102 will cause negative ions to collect around the tip of the gate 102, repelling negative ions within the ionic bath surrounding the tip, and consequently forming a depletion barrier. As a result of the decreasing number of ions of one polarity around the pore, the concentration of ions with the opposite polarity will also decrease in order to maintain electro-neutrality. The above behavior has the net effect of further suppressing ionic current in the channel. Alternately, when a positive potential is applied to gate 102, the zeta potential of the electric double layer and depletion barrier recedes, and the flow of ions between source 104 and drain 106 is enhanced.

In an exemplary embodiment, the gate 102 may be comprised of chromium, which adheres well to glass, and forms a consistent, continuous coating. However, in alternative embodiments the gate 102 may be made out of copper, aluminum, or any other conductive or semi-conductive material that would allow the gate 102 to maintain a certain potential.

Returning to FIG. 1, source and gate 102 may be attached to the same voltage 108 source or independent voltage sources. If the source and gate 102 are attached to the same voltage source 108, intervening circuitry may be implemented so that the voltage applied to the source 104 and gate 102 may be adjusted independently. Furthermore, a current amplifier may be applied to source electrode 104.

Furthermore, as shown in FIG. 1, the capillary pipette 100 may further comprise an insulator 100 covering the gate 102 to prevent the gate 102 from shorting if the pipette 100 is immersed in bath of ionic solution.

Figure 4:
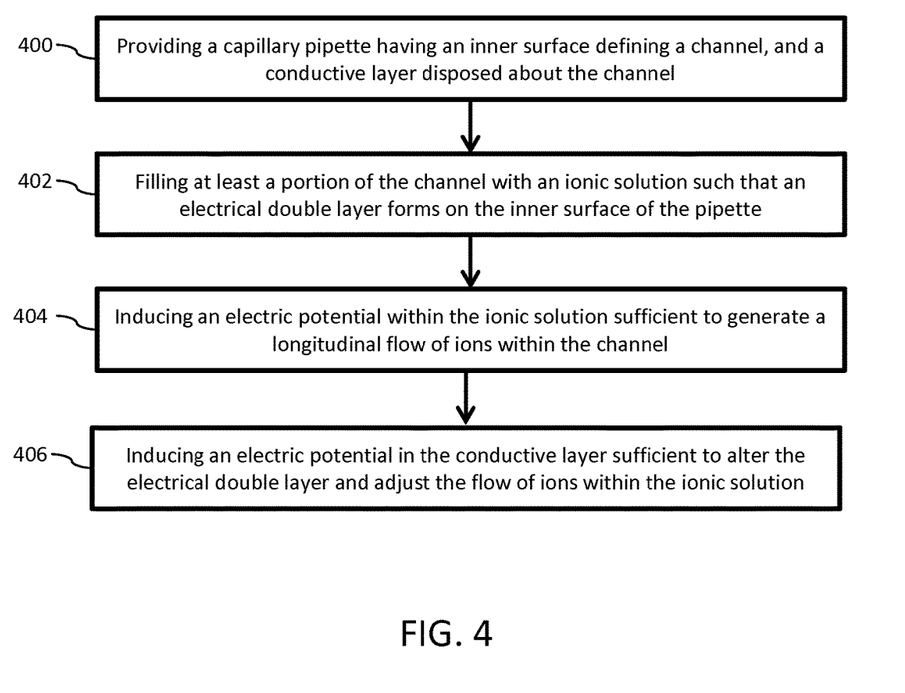
FIG. 4 shows a block diagram of a method according to an embodiment of the present invention.

FIG. 4 shows a method of practicing the present invention, according to an illustrative embodiment. In step 400, a capillary pipette 100 is provided, wherein at least a portion of the pipette 100 is covered in a conductive layer. The capillary pipette 100 has an inner surface defining a channel. In step 402, at least a portion of the channel is filled with an ionic solution, forming an electric double layer within the capillary pipette 100. In step 404, a source and drain 106 is provided to create a potential difference within the capillary pipette 100. The source and drain 106 may be positioned anywhere within capillary pipette 100 sufficient to create a potential difference within the ionic solution and through at least a portion of the pipette 100. Specifically, the source and drain 106 are positioned to generate a longitudinal flow of ions through the capillary pipette 100—in other words, to generate a current flowing through the pipette 100 which may be adjusted by applying a voltage to the gate 102 in later steps. For example, as shown in FIG. 1, if capillary pipette 100 is placed in a bath of ionic solution, the source could be place in the top of the pipette 100, while the drain 106 could be located within the bath of ionic solution. In step 406, a voltage is applied to conductive layer 102 to control ionic flow through the pipette 100 by altering the width of the electric double layer. This step may include the step of first attaching the voltage source of the conductive layer. Furthermore, as described above, different polarity voltages may be applied to alternately strengthen or weaken the electric double layer and modify the flow of current.

As an example of the above device and method, a capillary pipette 100 was fabricated from borosilicate glass capillaries with initial inner diameter 0.5 mm and outer diameter 1 mm. Pulling was performed with commercial puller P-2000 ("Sutter, Novato", Calif.). Prior to pulling, capillaries were cleaned thoroughly with alcohol. The tip diameter of the nanopore and wall thickness after pulling was determined by Scanning Electron Microscopy (SEM) images, because wall thickness can vary depending on pulling settings, especially temperature. Pipettes 100 with 60 nm pore diameter were used, and each having a wall thickness about 25-30 nm at the tip. A 15 nm thick film of Chromium on outer wall of pipette 100 served as a Gate 102 electrode. Deposition of chromium was performed using the electron beam evaporation technique, with pipette 100 tip slightly tilted upwards to prevent blocking and deposition inside the pore. Different thicknesses of Cr layers were tested, from 5 nm to 50 nm. Layers thicker than 30 nm often blocked the pore, whereas, films below 10 nm were mechanically unstable. After Cr deposition, micropipette 100 tip was coated with polymer by dipping it in a photoresist solution. In order to remove excessive polymer and make the coating uniform, pipette 100 was placed into a spinner and centrifuged for 60 seconds. After that, to prevent blockade of the pore, the pipette 100 was connected to air pump with flow direction from narrow to wide opening. As a final step, to solidify photoresist, the pipette 100 was baked at 120 degrees Celsius for 2 minutes.

The coated micropipette 100, described above, was filled with sodium chloride solution and immersed in the bath with the same solution. An Ag/AgCl measurement electrode (source electrode) was placed inside pipette 100, and reference electrode (drain electrode 106) immersed into the bath solution close to capillary tip. A gate 102 electrode was attached to pipette 100 coated with Cr, above the layer of photoresist. To record the source 104-drain 106 current, an Axopatch 200B amplifier was used in voltage clamp mode with a low-pass Bessel filter at 2 or 5 kHz bandwidth. The signal was digitized by an Axon Instruments Digidata 1440A with sampling rate 250 kHz, and recorded by AxoScope 10.2 (Axon Instruments, USA). The Axopatch amplifier also serves as a voltage source between source 104 and drain 106 electrodes. The gate 102 was applied by regulated DC power supply. A picoammeter was connected in series with the gate 102 in order to measure leakage current.

Figure 5A:
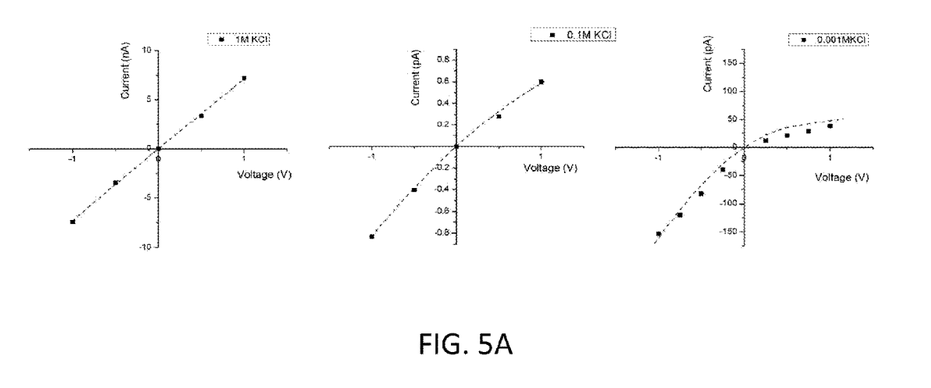
FIG. 5A shows a graph according to an embodiment of the present invention showing current through a pipette 100 without a voltage applied to the gate 102.

FIG. 5A shows the results of the applying a voltage between the source and drain 106, without a potential applied to the gate 102. Positive current through the pore was established when positive voltage was applied to the Source electrode 104 with respect to grounded Drain 106 electrode. This means that positive potassium ions drifted from the wide opening of pipette 100 to small opening. The $I_{SD}$-$V_{SD}$ curve was measured for potentials from −1 V to 1V with interval of 100 mV, for three different KCl concentrations 1 M, 0.1 M, 0.001 M and zero Gate 102 voltage. For all concentrations pH value was buffered to 7. High concentrations show almost linear dependence, when low concentrations present rectification phenomena: allowing more current to flow in one direction than the other. Current flow through the pipette 100 pore has a preferable direction from small opening to wide, while current in reverse direction is suppressed.

Figure 5B:
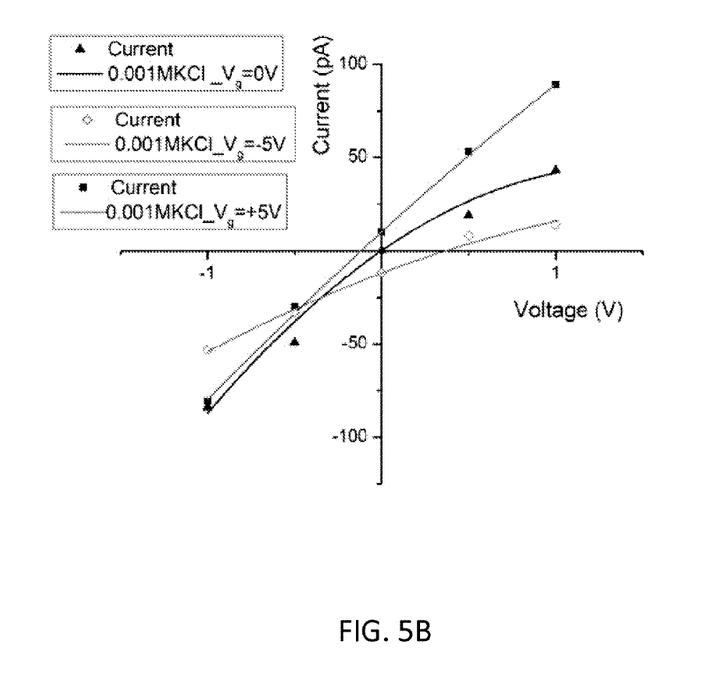
FIG. 5B shows a graph according to an embodiment of the present invention showing current through a pipette 100 with a voltage applied to the gate 102.

FIG. 5B shows the results of the example with a gate 102 voltage applied. Gate 102 voltage ($V_G$) was introduced with no potential difference between Source and Drain 106 ($V_{SD}$=0 v). Leakage current between Gate 102 and Source ($I_{leak}$) did not exceed 15 pA for $V_G$=±5 V. $I_{SD}$-$V_{SD}$ dependence for three different Gate 102 potentials is presented on for $V_G$=0 we observed typical I-V curve for conical capillary pore. For positive potential, which is increasing from $V_{SD}$=0 V to $V_{SD}$=+1 V, current through nanochannel will saturate and $I_{SD}$=43 pA. While for reverse potential, which decreased from $V_{SD}$=0 V to $V_{SD}$=−1 V, current showed almost linear dependence and $I_{SD}$=−84 pA. The rectification ratio, which can be calculated as ratio of channel conductance at $V_{SD}$=+1V to channel conductance at $V_{SD}$=−1 V, was equal to 0.51.

For $V_G$=−5 V even more current suppression for positive voltage was observed. Current saturated and reached value $I_{SD}$=31 pA for $V_{SD}$=+1 V. However, for negative Source-Drain 106 voltage current suppression was more significant and $I_{SD}$ equaled −41 pas for $V_{SD}$ equal to −1 V. Therefore, rectification ratio increased to the value 0.76. For $V_G$ equal to +5 V, the opposite behavior was observed. The positive gate 102 potential strongly affected positive current, raising conductance and having almost no effect on negative voltage current. When $V_{SD}$=+1 V current between Source and Drain 106 electrodes rose to $I_{SD}$=79 pA, and for $V_{SD}$=−1 V current was $I_{SD}$ equal to 90 pA. In this case rectification ratio was 0.88.

What is claimed is:

1. A method for controlling the transport of ions through a channel, comprising the steps of:
   providing a capillary pipette having a narrow portion with an inner surface defining a channel, wherein the narrow portion terminates at a tip having an end, one or more voltage sources connected to a first electrode and a second electrode, the first electrode within the channel, and a conductive layer disposed along the narrow portion and extending to the end of the tip;
positioning at least a part of the narrow portion in a bath of an ionic solution;
wherein the second electrode extends at least partially into the bath of the ionic solution, directly exposed to the ionic solution;
filling at least a portion of the channel with the ionic solution such that an electrical double layer forms on the inner surface of the pipette;
wherein the flow of all moving ions in the ionic solution is only toward the tip of the narrow portion;
inducing an electric potential within the ionic solution, between the first and second electrodes, sufficient to generate a longitudinal flow of ions within the channel;
wherein the moving ions exit the capillary pipette at the tip of the narrow portion; and
inducing an electric potential in the conductive layer sufficient to alter the electrical double layer and adjust the flow of ions within the ionic solution.

2. The method of claim 1, wherein the capillary pipette is dimensioned such that the electric double layer overlaps at at least one point.

3. The method of claim 1, wherein the capillary pipette is dimensioned such that the electric double layer will overlap at at least one point upon the application of a predetermined potential to the conductive layer.

4. The method of claim 1, wherein the pipette is dimensioned to narrow at at least one point.

5. The method of claim 4, wherein the narrow point of the pipette is minimally 10 nm in diameter and maximally 100 nm in diameter.

6. The method of claim 4, wherein the narrow point is at a tip of the pipette.

7. The method of claim 1, wherein the potential applied to the conductive layer causes the electrical double layer to widen, reducing the flow of ions within the channel.

8. The method of claim 1, wherein the potential applied to the conductive layer causes the electrical double layer to narrow, enhancing the flow of current within the channel.

9. The method of claim 1 wherein said conductive layer is comprised of one of chromium, aluminum, copper, or any other material capable of retaining a charge.

10. A device for controlling the transport of ions through a channel, comprising:
a capillary pipette having a narrow portion with an inner surface defining a channel;
wherein the narrow portion terminates at a tip having an end;
one or more voltage sources connected to a first electrode and a second electrode, the first electrode within the channel;
wherein the pipette is adapted to form an electric double layer on the inner surface when filled with an ionic solution;
wherein the device is configured to control the flow of all moving ions in the ionic solution to only toward the tip of the narrow portion;
a bath of the ionic solution, wherein at least part of the narrow portion is submerged within the ionic solution and the second electrode extends at least partially into the bath of the ionic solution, directly exposed to the ionic solution; and
a conductive layer positioned along the narrow portion, extending to the end of the tip, to exhibit an electric field within the channel when subjected to an electric charge, such that any electric double layer on the inner surface will be altered by the electric field;
wherein the device is configured so that all moving ions exit the capillary pipette at the tip of the narrow portion.

11. The device of claim 10, further comprising a voltage source positioned to induce a longitudinal flow of ions in any ionic fluid at least partially filling the channel.

12. The device of claim 10, further comprising a voltage source connected to apply a potential to the conductive layer.

13. The device of claim 10 wherein the capillary pipette is dimensioned to cause the electric double layer to overlap when the channel is filled with an ionic solution.

14. The device of claim 10 wherein the capillary pipette 100 is dimensioned to cause the electric double layer to overlap when the channel is filled with an ionic solution and a predetermined potential is applied to the conductive layer.

15. The device of claim 10, wherein the capillary pipette is dimensioned to narrow at at least one point.

16. The device of claim 15, wherein the narrow point is at the tip of the pipette.

17. The device of claim 10, wherein the capillary pipette 100 is minimally 10 nm in diameter and maximally 100 nm in diameter.

18. The device of claim 10, wherein said conductive layer is comprised of one of chromium, aluminum, copper, or any other material capable of retaining a charge.

* * * * *

UNITED STATES PATENT AND TRADEMARK OFFICE
CERTIFICATE OF CORRECTION

PATENT NO. : 10,352,898 B2
APPLICATION NO. : 15/121440
DATED : July 16, 2019
INVENTOR(S) : Yauheni Rudzevich et al.

It is certified that error appears in the above-identified patent and that said Letters Patent is hereby corrected as shown below:

On the Title Page

Column 1, Line 14, Assignee name: delete the misspelled word "FOUNDAING" and insert:
--FOUNDATION--

Signed and Sealed this
Tenth Day of September, 2019

Andrei Iancu
*Director of the United States Patent and Trademark Office*